United States Patent
West

(10) Patent No.: US 6,579,622 B2
(45) Date of Patent: Jun. 17, 2003

(54) ACIDIC COPPER SALT-FATTY AMINE SALT WOOD PRESERVATIVE COMPOSITION AND METHOD

(76) Inventor: Michael Howard West, 54 S. Crockett Rd., Senatobia, MS (US) 38668

( * ) Notice: Subject to any disclaimer, the term of this patent is extended or adjusted under 35 U.S.C. 154(b) by 0 days.

(21) Appl. No.: 09/943,312

(22) Filed: Aug. 31, 2001

(65) Prior Publication Data

US 2003/0044629 A1 Mar. 6, 2003

(51) Int. Cl.⁷ .............................................. B32B 21/06
(52) U.S. Cl. .................... 428/535; 428/536; 428/537.1; 424/630; 424/632; 424/633; 424/634; 424/635; 424/637; 424/638; 514/75; 514/383; 514/642; 514/643; 514/500; 106/18.31; 106/18.32
(58) Field of Search ................................. 428/535, 536, 428/537.1; 424/630, 632, 633, 634, 635, 637, 636; 514/75, 383, 642, 643, 500; 106/18.31, 18.32

(56) References Cited

U.S. PATENT DOCUMENTS

| 5,276,029 | A | * | 1/1994 | Goettsche | 514/231.2 |
| 5,426,121 | A | * | 6/1995 | Bell | 514/500 |
| 5,444,093 | A | * | 8/1995 | Goettsche | 514/61 |
| 5,853,766 | A | * | 12/1998 | Goettsche | 424/632 |

* cited by examiner

Primary Examiner—Leszek Kiliman

(57) ABSTRACT

A wood preservative composition which comprises water soluble acidic copper salts plus water soluble fatty amine salts in a weight ratio of from 0.1 to 10 parts water soluble fatty amine salt for each part of water soluble acidic copper salt. Methods for protecting wood from termites, decay, and mildew, and for reducing the ferrous metal corrosion properties of water soluble copper salts by using the disclosed composition are provided.

5 Claims, No Drawings

ACIDIC COPPER SALT-FATTY AMINE SALT WOOD PRESERVATIVE COMPOSITION AND METHOD

CROSS REFERENCE TO RELATED APPLICATIONS-NOT APPLICABLE

STATEMENT REGARDING FEDERALLY SPONSORED RESEARCH OR DEVELOPMENT

NOT APPLICABLE

REFERENCE TO A MICROFICHE APPENDIX

NOT APPLICABLE

BACKGROUND OF THE INVENTION

The field of endeavor to which this invention pertains is the preparation and use of acidic copper wood preservatives with reduced ferrous metal corrosion properties and improved wood protection properties. The subject matter of the claimed invention relates to water soluble fatty amine salts, and their use with water soluble acidic copper wood preservative salts.

Amines are ammonia derivatives; they are obtained from ammonia by replacement of one, two or three of the hydrogens by alkyl groups. When at least one alkyl group is derived from a fatty acid, or synthesized to mimic a fatty acid alkyl group the amine is known as a fatty amine. Wood preservatives are most economically diluted with water for wood treating, and my invention is especially concerned with water soluble fatty amine salts. The formate salt of dimethylcocoamine is preferred in my invention.

Acidic copper wood preservative salts include the sulfate, formate, and acetate. In the prior art copper sulfate has been most used commercially; and almost invariably with chromates for inhibiting corrosion, and for fixing the copper in the wood. The formate and acetate are known to provide superior wood preservation when compared to the sulfate; however, they have been little used because of corrosion problems without chromates, and poor compatibility with chromates. Copper formate, because of its superior record of long term wood protection, is the preferred water soluble acidic copper salt in my invention.

Water soluble acidic copper salts and their superior wood protection properties are reported in the wood preservation technical literature. Water soluble fatty amine salts are also reported in the wood preservation technical literature. There are no reports of combining the two salts, or of the reduced corrosion properties and improved wood protection properties which results when the two are combined. With restrictions on the use of chromates in recent years, many new copper wood preservatives are being developed. Invariably, these new preservatives are complexes of copper compounds with ammonia or amines. The acid copper salts have been ignored for fear of corrosion problems even though it is known they can be used successfully at much lower copper retentions in the wood.

I have found that water soluble fatty amine salts are effective corrosion inhibitors for water soluble acidic copper salts, and that combinations of these two salts provide superior wood protection. It is anticipated my invention will be used with pressure treating.

BRIEF SUMMARY OF THE INVENTION

The present invention provides a novel wood preservative composition which comprises water soluble acidic copper salts combined with water soluble fatty amine salts in a weight ratio of from 0.1 to 10 parts water soluble fatty amine salt for each part of water soluble acidic copper salt. It also provides a method for protecting wood from attack by termites, decay, and mildew which comprises treating the wood to a retention of from 0.01 to 1 pound per cubic foot of a water soluble acidic copper salt plus 0.01 to 1 pound per cubic foot of a water soluble fatty amine salt. It further provides a method for reducing the ferrous metal corrosion properties of water soluble acidic copper wood preservative salts which comprises combining them with water soluble fatty amine salts wherein the weight ratio of the water soluble fatty amine salt to the water soluble acidic copper salt ranges from 0.1 to 10. The object of my invention is to allow the continued use of acidic copper salts, now without chromates, in wood preservation so as to conserve millions of pounds of copper, and to protect the environment from chromates and unnecessary copper.

DETAILED DESCRIPTION OF THE INVENTION

The preferred embodiment of my invention relates to the use of copper formate with dimethylcocoamine formate for wood preservation. Copper formate may be prepared by blending formic acid with a fixed copper salt, such as copper carbonate, in water; the ratio of the two components may vary from chemical equivalent if that is found desirable for wood treating. Dimethylcocoamine formate may be prepared by blending formic acid with dimethylcocoamine in water; again, the ratio of the components may vary from chemical equivalent if that is found desirable for wood treating. A combination of copper formate and dimethylcocoamine formate may be prepared in water by adding the copper carbonate and the formic acid and blending until the copper is in solution, then blending in the dimethylcocoamine.

Copper formate and copper formate plus dimethylcocoamine formate wood treating solutions were prepared according to the following six examples and used to treat southern yellow pine boards to retentions of approximately 40 pounds per cubic foot:

Example 1 Copper formate 0.5 pbw plus water 99.5 pbw.

Example 2 Copper formate 0.25 pbw plus dimethylcocoamine formate 0.25 pbw plus water 99.5 pbw.

Example 3 Copper formate 0.1 pbw plus dimethylcocoamine formate 1.0 pbw plus water 98.9 pbw.

Example 4 Copper formate 1.0 pbw plus dimethylcocoamine formate 0.1 pbw plus water 98.9 pbw.

Example 5 Copper formate 2.500 pbw plus dimethylcocoamine formate 0.025 pbw plus water 97.475 pbw.

Example 6 Copper formate 0.025 pbw plus dimethylcocoamine formate 2.500 pbw plus water 97.475 pbw.

The treated boards and untreated controls were placed on the ground for six months. At this time they were examined for termite, decay, and mildew attack. None of the treated boards exhibited termite or decay attack; those treated only with copper formate exhibited mildew attack. The untreated boards exhibited termite, decay and mildew attack.

Copper formate wood treating solutions and copper formate plus dimethylcocoamine formate wood treating solutions were examined for corrosion properties when placed in mild steel vessels. The copper formate solutions corroded the mild steel within 24 hours. None of the aqueous solutions containing dimethylcocoamine formate, even at the low ratio of 0.1 part for each part of copper formate, corroded the mild steel after six weeks.

It is preferred the compositions of my invention be impregnated in wood by pressure using a full cell type process. It is preferred that common mild steel fasteners be used for the treated wood. It is preferred that cationic paraffin wax emulsions be used with the treating solutions of my invention when the treated wood is to be exposed to the weather. It is proposed that compatible insecticides may be added to the treating solutions of my invention or to the composition concentrates of my invention.

I claim:

1. A wood preservative composition which comprises water soluble acidic copper salts plus water soluble fatty amine salts in a weight ratio of from 0.1 to 10 parts water soluble fatty amine salt for each part of water soluble acidic copper salt.

2. A composition according to claim 1 wherein the water soluble acidic copper salt comprises copper formate.

3. A composition according to claim 1 wherin the water soluble fatty amine salt comprises dimethylcocoamine formate.

4. A method for protecting wood from attack by termites, decay, and mildew which comprises treating the wood to a retention of from 0.01 to 1 pound per cubic foot of a water soluble acidic copper salt plus 0.01 to 1 pound per cubic foot of a water soluble fatty amine salt.

5. A method for reducing the ferrous metal corrosion properties of water soluble acidic copper wood preservative salts which comprises combining them with water soluble fatty amine salts wherein the weight ratio of the water soluble fatty amine salt to the water soluble acidic copper salt ranges from 0.1 to 10.

* * * * *